United States Patent [19]

Salmond

[11] 4,006,172

[45] Feb. 1, 1977

[54] PROCESS FOR 7-KETO-$\Delta^5$-STEROIDS

[75] Inventor: William G. Salmond, Kalamazoo, Mich.

[73] Assignee: The Upjohn Company, Kalamazoo, Mich.

[22] Filed: Apr. 26, 1976

[21] Appl. No.: 680,022

[52] U.S. Cl. .......................... 260/397.2; 260/397.4
[51] Int. Cl.$^2$ .......................................... C07J 9/00
[58] Field of Search ...................... 260/397.2, 397.4

[56] References Cited

UNITED STATES PATENTS 3,966,777  6/1976  Mazur et al. .................. 260/397.2

Primary Examiner—Elbert L. Roberts
Attorney, Agent, or Firm—Bruce Stein; Roman Saliwanchik

[57] ABSTRACT

Disclosed is an improved process for the oxidation of certain $\Delta^5$-steroids to the corresponding 7-keto-$\Delta^5$-steroids by use of a chromium trioxide-pyrazole oxidant (oxidizing agent).

12 Claims, No Drawings

PROCESS FOR 7-KETO-Δ⁵-STEROIDS

BACKGROUND OF THE INVENTION

The transformation of a $\Delta^5$-steroid to a 7-keto-$\Delta^5$-steroid has long been known in the steroid literature as a desirable means for the preparation of intermediates which are then converted to many other pharmaceutically useful steroids. For example, cholesteryl acetate is transformed to 7-ketocholesteryl acetate. See Dauben, et al. J. Org. Chem. 34, 3587 (1969). The intermediate 7-ketocholesteryl esteryl is then converted to cholesta-5,7-diene-3-ol 3-acetate (provitamin $D_3$) see Dauben, et al. J. Org. Chem. 36, 3277 (1971). Provitamin $D_3$ is then converted to Vitamin $D_3$ by methods well known to those skilled in the art.

Similarly 17α-methyl-androsta-5-ene-7-one-3β,17β-diol diacetate is formed by the oxidation of 17α-methyl-androsta-5-ene-3β,17β-diol diacetate. 17α-methyl-androsta-5-ene-7-one-3β,17β-diol diacetate is then converted to calusterone (7β,17α-dimethyltestosterone) a useful anabolic agent and gonadatropin inhibitor. See U.S. Pat. No. 3,654,320.

The known methods for oxidizing $\Delta^5$-steroids to 7-keto$\Delta^5$-steroids include sodium chromate in conjunction with acetic anhydride and acetic acid but this demands long reaction time and undesirable by-products are formed. t-Butyl chromate has also been used but this is a hazardous reagent and is best avoided. Bispyridine chromium trioxide is known to achieve the oxidation cleanly, but again reaction times are long and large excesses of chromium reagent are required. In short the oxidation methods available are either hazardous, time consuming or inconvenient in their use.

A chromiun trioxide-pyrazole complex has been described as a reagent for the oxidation of alcohols. See Corey and Fleet, Tetrahedyron Letters 4499 (1973).

The surprising discovery has been made that a chromium trioxide-pyrazole complex serves as an efficient oxidizing agent for the allylic oxidation of a $\Delta^5$-steroid. This oxidation is accomplished best at low temperatures in a few hours. The work-up is simple and the pyrazole is readily recovered.

BRIEF SUMMARY OF THE INVENTION

Disclosed is an improved chemical process for the production of a steroid of the formula

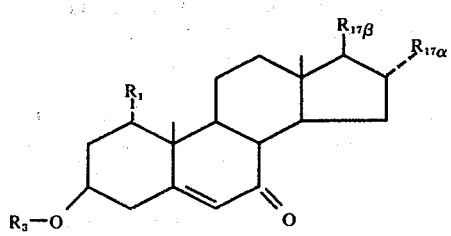

where $R_1$ is hydrogen, alkanoyloxy of 1 thru 6 carbon atoms or benzoyloxy, where $R_3$ is alkanoyl of 1 thru 6 carbon atoms or benzoyl; $R_{17\,\alpha}$ is hydrogen or methyl and $R_{17\,\beta}$ is

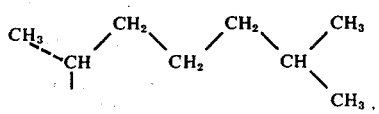

-continued

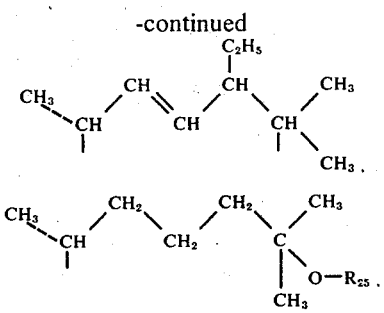

hydroxy or acetoxy where $R_{25}$ is hydrogen, alkanoyl of 1 thru 6 carbon atoms or benzoyl with the provisos that (1) when $R_{17\,\alpha}$ is hydrogen, $R_{17\,\beta}$ is

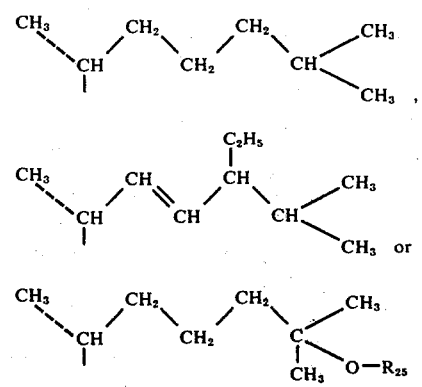

where $R_{25}$ is defined above and (2) when $R_{17\,\alpha}$ is methyl, $R_{17\,\beta}$ is hydroxy or acetoxy, where a compound of the formula

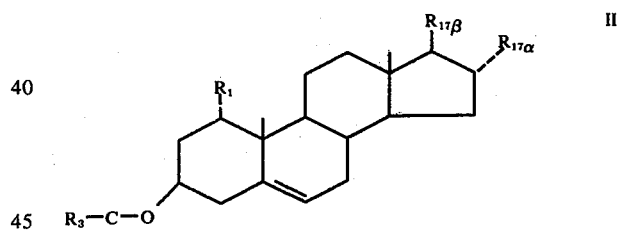

where $R_1$, $R_3$, $R_{17\,\alpha}$ and $R_{17\,\beta}$ are defined above is oxidized at the C-7 position by an oxidizing agent followed by extraction and purification where the improvement comprises using a complex of chromium trioxide and a substituted pyrazole of the formula

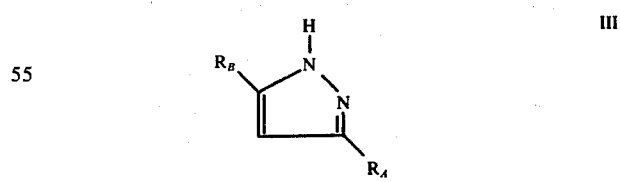

as the oxidizing agent where $R_A$ and $R_B$ can be the same or different and are hydrogen, methyl or phenyl.

It is preferred that the oxidizing agent be 3,5-dimethylpyrazole chromium trioxide.

DETAILED DESCRIPTION OF THE INVENTION

The improved chemical process of this invention is very useful in producing 7-keto-$\Delta^5$-steroids within the scope of formula I which are intermediates useful in production of various pharmaceuticals. For example, 7-ketocholesteryl acetate (claim 4) is transformed to Vitamin $D_3$. See Dauben, et al. J. Org. Chem. 34, 3587 (1969) and J. Org. Chem. 36, 3277 (1971). Additionally 17α-methyl-androsta5-ene-7-one-3β,17β-diol diacetate (claim 10) is transformed to calusterone. See U.S. Pat. No. 3,654,320.

The improved process of the present invention is performed as described below.

The chromium trioxide-pyrazole oxidant is prepared by adding the pyrazole to a suspension of an equal molar quantity of chromium trioxide in a solvent such as methylene chloride, chloroform or benzene. It is preferred that the solvent be methylene chloride. The mixture is stirred for 15 minutes at a temperature of $-40°$ to $40°$. It is preferred that the temperature be in the range of $-25°$ to $-15°$. After the solution of the oxidant is stirred for about 15 minutes, the steroid is added and the reaction mixture stirred until the reaction is complete as measured by TLC (thin-layer chromatography). The reaction time may be as short as one-half hour or up to about 24 hours but usually is in the range of 2–6 hours. The reaction mixture is stirred preferably in a temperature range of $-25°$ to $-15°$. Although the oxidation of a $\Delta^5$-steroid to the corresponding 7-keto-$\Delta^5$steroid proceeds readily at room temperature, less chromium trioxide-pyrazole complex is required if the reaction is conducted in the temperature range of $-25°$ to $-15°$.

Following completion of the reaction as measured by TLC, the work-up is conducted in a manner that allows for the isolation of the pyrazole. This permits recycling of the pyrazole, an advantage in a manufacturing process. The work-up is most conveniently done by stirring the oxidation reaction mixture with a basic solution (sodium hydroxide). This causes decomposition of the chromium trioxide-pyrazole complex with the chromium salts dissolving in the aqueous phase and the pyrazole and steroid in the organic layer. The pyrazole and the steroid are then separated in a routine fashion by acid extraction of the pyrazole. The pyrazole is recovered by basification of the acidic extract using conventional techniques. The steroid is purified by means well known to those skilled in the art.

The compounds of formula I produced by the improved process of the present invention have varying substitution of $R_1$, $R_3$, $R_{17 \alpha}$, $R_{17 \beta}$, $R_A$ and $R_B$ as defined previously. Examples of alkanoyloxy of 1 thru 6 carbon atoms are formyloxy, acetoxy, propionyloxy, butanoyloxy, pentanoyloxy, hexanoyloxy and isomers thereof. Examples of alkanoyl of 1 thru 6 carbon atoms are formyl, acetyl, propionyl, butanoyl, pentanoyl, hexanoyl and isomers thereof.

The invention may be better understood from the following examples.

All temperatures are in degrees centigrade.

Saline refers to an aqueous saturated sodium chloride solution.

NMR refers to nuclear magnetic resonance.

NMR spectra are recorded on a Varian A-60 spectrophotometer with tetramethylsilane as an internal standard.

Melting points are determined on a Thomas-Hoover melting point apparatus.

Preparation 1 - Stigmasteryl Benzoate (Formula II; $R_1$ and $R_{17 \alpha}$ are hydrogen, $R_3$ is benzoyl and $R_{17 \beta}$ is

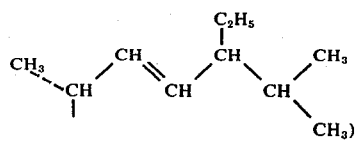

Stigmasterol (250 g) is dissolved in warm (45°–60°) pyridine (350 ml). Benzoyl chloride (100 ml) is added dropwise to the stirred solution of stigmasterol in pyridine. The resulting mixture is stirred for 1 hour and then poured into 2000 ml of water. The precipitated crystals are filtered and washed with water. The crystals are dissolved in warm (45°–60°) chloroform, washed successively with dilute hydrochloric acid and saturated sodium bicarbonate. The solution is then concentrated to a volume of 750 ml and then 750 ml of methanol is added. Stigmasteryl benzoate crystallizes and after cooling is filtered to give 305 g of the title compound m.p. 158°–160°.

EXAMPLE 1

7-Ketostigmasteryl Benzoate (Formula I: $R_1$ and $R_{17 \alpha}$ are hydrogen, $R_3$ is benzoyl, $R_{17 \beta}$ is

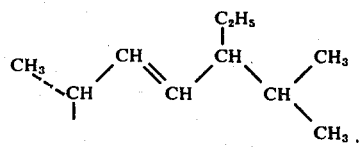

$R_A$ and $R_B$ are methyl).

Chromium trioxide (6.25 g) is stirred in methylene chloride (50 ml) at $-20°$. 3,5-Dimethylpyrazole (5.6 g) is added to the chromium trioxide suspension. After 15 minutes of stirring, stigmasteryl benzoate (Preparation 1) is added and the mixture stirred for 4 hours at $-20°$ to $-10°$. Sodium hydroxide (25 ml 5N) is then added and the mixture stirred for about 1 hour at 0°. The phases are then separated. The organic layer is washed with dilute hyrochloric acid, saline, dried, and concentrated to yield a crystalline residue. The crystalline residue is recrystallized from cyclohexane to give the title compound. m.p. 171°–172°; NMR (CDCl$_3$ — 1% TMS)δ 0.71, 1.25, 5.13, 5.75, 7.5 and 8.03.

Following the procedure of Example 1 but substituting the $\Delta^5$-steroids of Column A for stigmasteryl benzoate there are obtained the corresponding 7-keto-$\Delta^5$-steroid products of Column B.

| Example | REACTANT (Col.A) $\Delta^5$-Steroid | PRODUCT (Col. B) 7-Keto-$\Delta^5$-Steroid |
|---|---|---|
| 2 | cholesteryl acetate | 7-ketocholesteryl acetate |
| 3 | 1α,3β-dihydroxy-$\Delta^5$-cholestadiol-dibenzoate | 1α,3β-dihydroxy-$\Delta^5$-7-ketocholestadiol-dibenzoate |

-continued

| Example | REACTANT (Col.A)<br>$\Delta^5$-Steroid | PRODUCT (Col. B)<br>7-Keto-$\Delta^5$-Steroid |
|---|---|---|
| 4 | 1α,3β,25-trihydroxy-$\Delta^5$-cholestatriol-triacetate | 1α,3β,25-trihydroxy-$\Delta^5$-7-ketocholestatriol-triacetate |
| 5 | 1α,3β,25-trihydroxy-$\Delta^5$-cholestatriol-1,3-dibenzoate | 1α,3β,25-trihydroxy-$\Delta^5$-7-ketocholestatriol-1,3-dibenzoate |
| 6 | 3β,25-dihydroxy-66 $^5$-cholestadiol-diacetate | 3β,25-dihydroxy-$\Delta^5$-7-ketocholestadiol-diacetate |
| 7 | 3β,25-dihydroxy-$\Delta^5$-cholestadiol-3-acetate | 3β,25-dihydroxy-$\Delta^5$-7-ketocholestadiol-3-acetate |
| 8 | 17α-methyl-androsta-5-ene-3β,17β-diol-diacetate | 17α-methyl-androsta-5-ene-7-one-3β,17β-diol-diacetate |
| 9 | 17α-methyl-androsta-5-ene-3β,17β-diol-3-acetate | 17α-methyl-androsta-5-ene-7-one-3β,17β-diol-3-acetate |

The reactants of Column A are either known to those skilled in the art or can readily be prepared by methods well known to those skilled in the art from compounds known to those skilled in the art.

I claim:
1. An improved chemical process for the production of a steroid of the formula

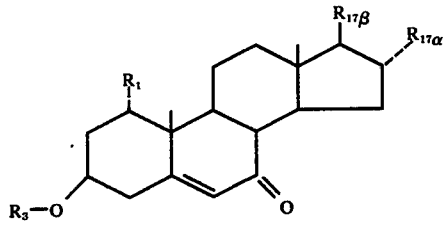
I where $R_1$ is hydrogen, alkanoyloxy of 1 thru 6 carbon atoms or benzoyloxy; where $R_3$ is alkanoyl of 1 thru 6 carbon atoms or benzoyl; $R_{17\alpha}$ is hydrogen or methyl and $R_{17\beta}$ is

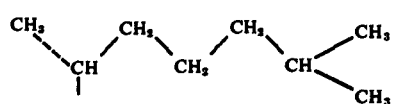

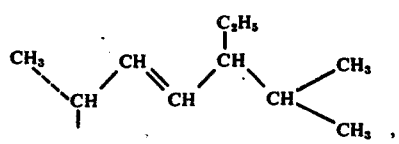

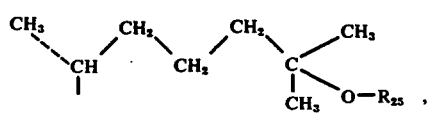

hydroxy or acetoxy where $R_{25}$ is hydrogen, alkanoyl of 1 thru 6 carbon atoms or benzoyl with the provisos that (1) when $R_{17\alpha}$ is hydrogen, $R_{17\beta}$ is

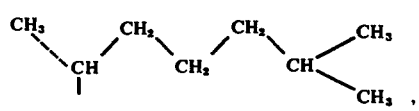

-continued
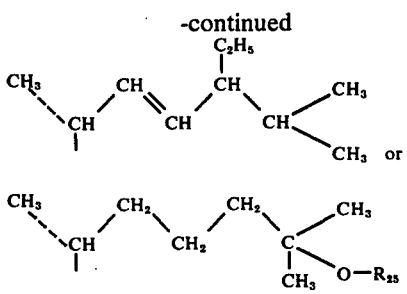

where $R_{25}$ is defined above and (2) when $R_{17\alpha}$ is methyl, $R_{17\beta}$ is hydroxy or acetoxy, where a compound of the formula

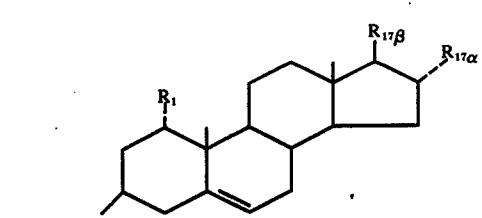
II where $R_1$, $R_3$, $R_{17\alpha}$ and $R_{17\beta}$ are defined above is oxidized at the C-7 position by an oxidizing agent followed by extraction and purification where the improvement comprises using a complex of chromium trioxide and a substituted pyrazole of the formula

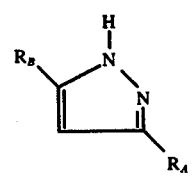
III as the oxidizing agent where $R_A$ and $R_B$ can be the same or different and are hydrogen, methyl or phenyl.

2. A process according to claim 1 where the oxidizing agent III is 3,5-dimethylpyrazole chromium trioxide.

3. A process according to claim 2 where the steroid I is 7-ketostigmasteryl benzoate.

4. A process according to claim 2 where the steroid I is 7-ketocholesteryl acetate.

5. A process according to claim 2 where the steroid I is 1α,3β-dihydroxy-Δ⁵-7-ketocholestadiol-dibenzoate.

6. A process according to claim 2 where the steroid I is 1α,3β,25-trihydroxy-Δ⁵-7-ketocholestatriol-triacetate.

7. A process according to claim 2 where the steroid I is 1α,3β,25-trihydroxy-Δ⁵-7-ketocholestatriol-1,3-dibenzoate.

8. A process according to claim 2 where the steroid I is 3α,25-dihydroxy-Δ⁵-7-ketocholestadiol-diacetate.

9. A process according to claim 2 where the steroid I is 3α,25-dihydroxy-Δ⁵-7-ketocholestadoil-3-acetate.

10. A process according to claim 2 where the steroid I is 17α-methyl-androst-5-ene-7-one-3β,17β-diol-diacetate.

11. A process according to claim 2 where the steroid I is 17α-methyl-androst-5-ene-7-one-3β,17β-diol-3-acetate.

12. An improved chemical process for the production of 7-ketostigmasteryl benzoate where stigmasteryl benzoate is oxidized at the C-7 position by an oxidizing agent followed by extraction and purification where the improvement comprises using 3,5-dimethylpyrazole chromium trioxide as the oxidizing agent.

* * * * *

UNITED STATES PATENT OFFICE
CERTIFICATE OF CORRECTION

Patent No. 4,006,172         Dated February 1, 1977

Inventor(s)    William G. Salmond           Page 1 of 4

It is certified that error appears in the above-identified patent and that said Letters Patent are hereby corrected as shown below:

Column 1, line 12, "7-ketocholesteryl esteryl" should read --7-ketocholesteryl--; line 19, "methyl" should read --Methyl--; line 25, "keto$\Delta^5$-" should read -- keto-$\Delta^5$- --; lines 50-55, the formula

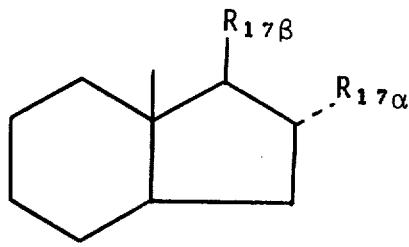

should read

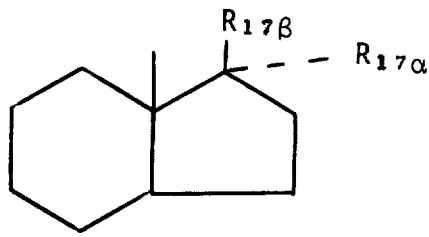

Column 2, line 15, "6carbon" should read --6 carbon--; lines 38-42, the formula

UNITED STATES PATENT OFFICE
CERTIFICATE OF CORRECTION

Patent No. 4,006,172    Dated February 1, 1977

Inventor(s)    William G. Salmond    Page 2 of 4

It is certified that error appears in the above-identified patent and that said Letters Patent are hereby corrected as shown below:

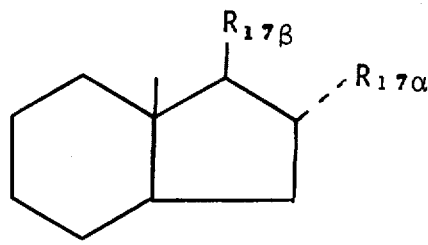

should read

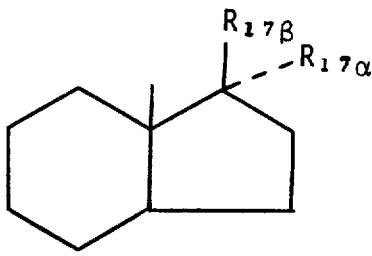

Column 3, line 6, "androsta5-" should read -- androsta-5- --; line 27, "$\Delta^5$steroid" should read --$\Delta^5$-steroid--. Column 5, under REACTANT (Col. A), "-66$^5$-" should read -- -$\Delta^5$- --; lines 30-35, the formula

UNITED STATES PATENT OFFICE
CERTIFICATE OF CORRECTION

Patent No. __4,006,172__  Dated __February 1, 1977__

Inventor(s) __William G. Salmond__  Page 3 of 4

It is certified that error appears in the above-identified patent and that said Letters Patent are hereby corrected as shown below:

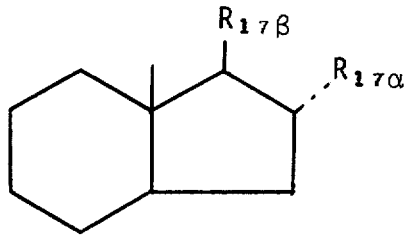

should read

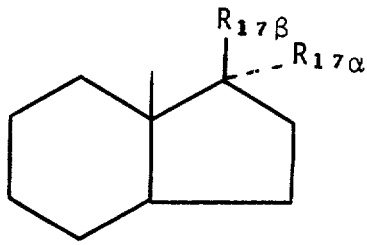

Column 6, lines 38-42, the formula

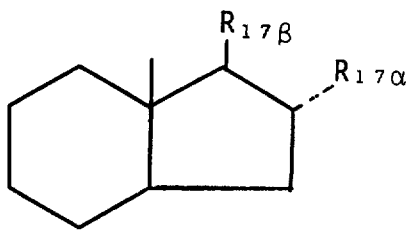

UNITED STATES PATENT OFFICE
CERTIFICATE OF CORRECTION

Patent No. 4,006,172    Dated February 1, 1977

Inventor(s) William G. Salmond

It is certified that error appears in the above-identified patent and that said Letters Patent are hereby corrected as shown below:

should read

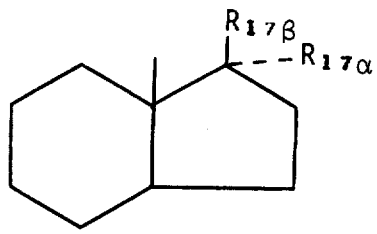

Column 7, line 10, "3α,25-" should read -- 3β,25- --; line 12, "3α,25-" should read -- 3β,25- --; line 12, "ketocholestadoil" should read --ketocholestadiol--.

Signed and Sealed this

Fourteenth Day of June 1977

[SEAL]

Attest:

RUTH C. MASON
Attesting Officer

C. MARSHALL DANN
Commissioner of Patents and Trademarks